Figure 1:
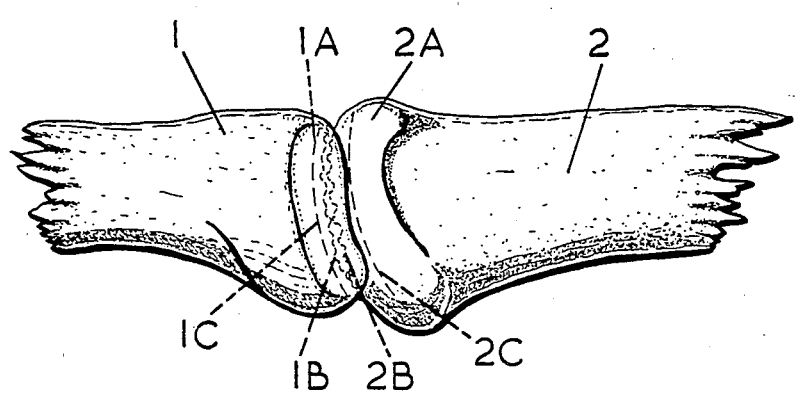

United States Patent [19]

Sully et al.

[11] 4,385,404

[45] May 31, 1983

[54] DEVICE AND METHOD FOR USE IN THE TREATMENT OF DAMAGED ARTICULAR SURFACES OF HUMAN JOINTS

[75] Inventors: Lance Sully, Sutton Bonnington, England; Ian T. Jackson, Rochester, Minn.

[73] Assignee: J. & P. Coats, Limited, Glasgow, Scotland

[21] Appl. No.: 236,976

[22] Filed: Feb. 23, 1981

[30] Foreign Application Priority Data

Feb. 21, 1980 [GB] United Kingdom ............... 8005826

[51] Int. Cl.³ .............................................. A61F 1/24
[52] U.S. Cl. ..................................... 3/1.91; 128/92 C
[58] Field of Search .................................. 3/1.9–1.913; 128/92 C, 92 CA

[56] References Cited

U.S. PATENT DOCUMENTS 3,879,767 4/1975 Stubstad ............................... 3/1.91

FOREIGN PATENT DOCUMENTS 876739 5/1953 Fed. Rep. of Germany ....... 3/1.913
1061009 11/1953 France ................................ 128/92 C
1122634 5/1956 France ............................... 128/92 CA

OTHER PUBLICATIONS

"Arthroplasty of the Hip-A New Operation", by John Charnley, The Lancet, May 27, 1961, pp. 1129–1132.

Primary Examiner—Ronald L. Frinks
Attorney, Agent, or Firm—William R. Hinds

[57] ABSTRACT

A device for treating a human joint having damaged articular surfaces, for example an arthritic joint, comprises a cap of concavo-convex lenticular form and constructed of a bio-compatible material. The function of the cap is to mould cartilage covering the damaged articular surfaces. The radius of curvature of the convex surface and of the concave surface may be numerically the same or the radius of the convex surface may be greater than the radius of the concave surface according to the particular joint to be treated.

3 Claims, 6 Drawing Figures

DEVICE AND METHOD FOR USE IN THE TREATMENT OF DAMAGED ARTICULAR SURFACES OF HUMAN JOINTS

This invention relates to a device for treating damaged articular surfaces in human joints and also to a method of using the device.

It has been known for some time that perichrondrium taken from part of the human body and grafted to another part of the human body is capable of producing new cartilage. This discovery has not, heretofore been of much use by itself because even if perichondrium were grafted on to an arthritic joint the result was a joint which, while new cartilage grew on the joint surfaces, was not capable of articulation because of the uncontrolled form of the cartilage growth.

It is an object of the present invention to provide a device which controls the shape of the growth of cartilage and it is also an object of the invention to provide a method for the use of such a device so that a joint having damaged articular surfaces, following infection, trauma or arthritis can be returned to or almost to its original condition.

A device for use in the treatment of a joint having damaged articular surfaces according to the invention comprises a cap of concavo-convex lenticular form and constructed of a bio-compatible flexible material.

The radius of curvature of the convex surface and of the concave surface may be the same or the radius of the convex surface may be greater than the radius of the concave surface.

Bio-compatible materials suitable for making such a cap are elastomeric materials such as polyurethane or natural or synthetic rubber.

The device of the invention and a method of using the device will now be described with reference to the accompanying drawings.

Figure 2:
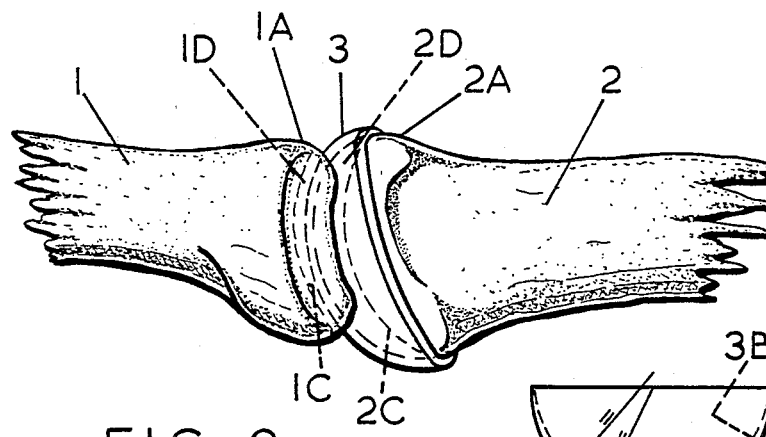
Figure 6:
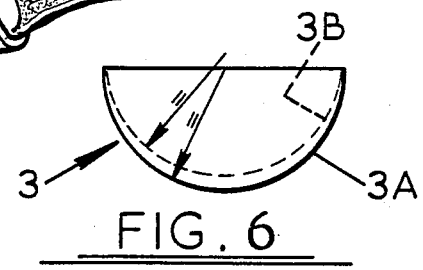
Figure 3:
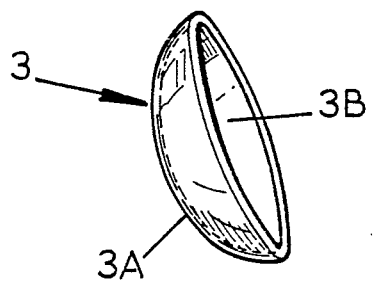
Figure 4:
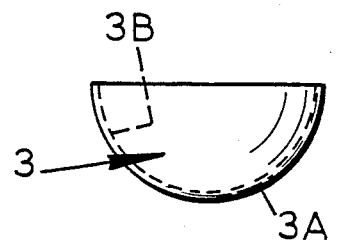
Figure 5:
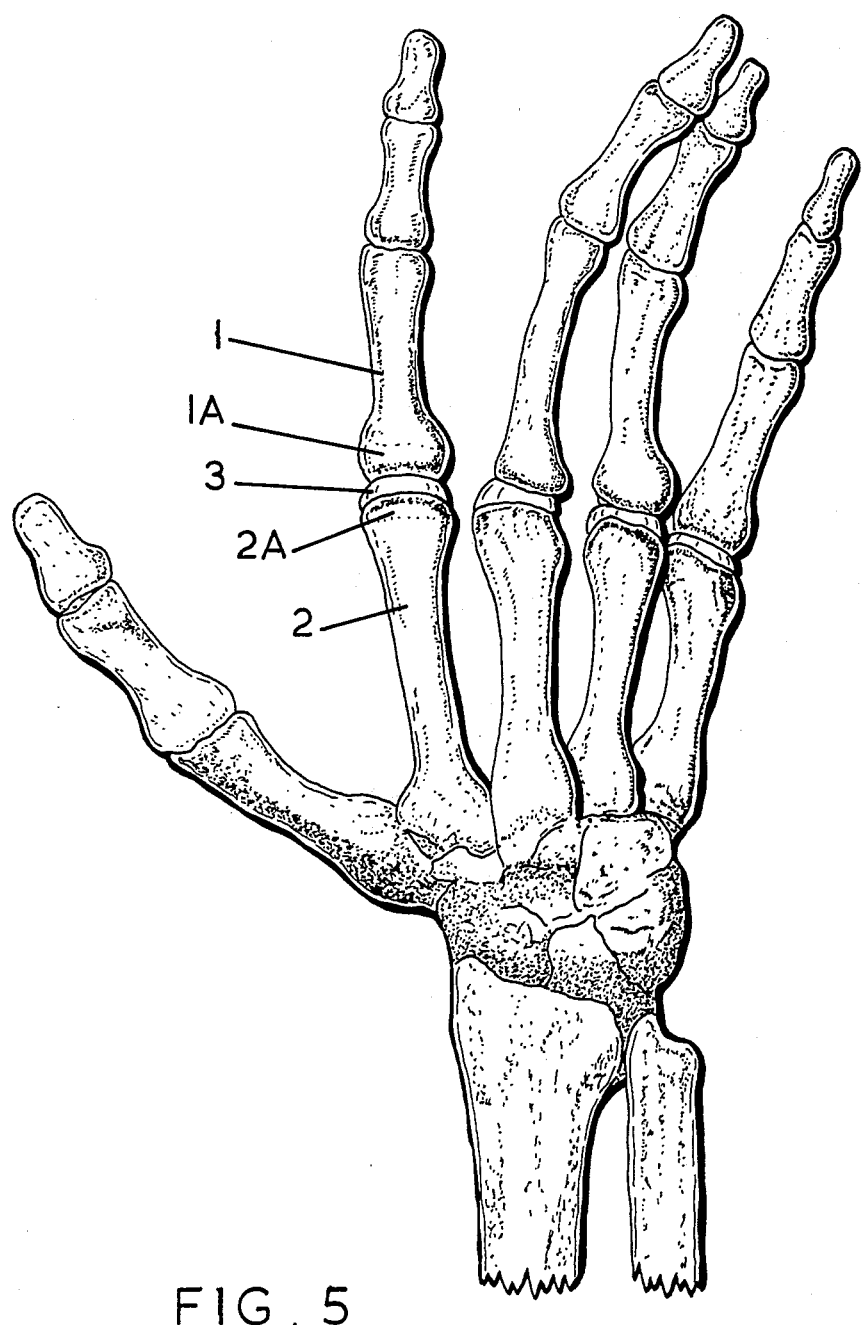

In these drawings FIG. 1 shows a damaged joint,

FIG. 2 shows a metacarpo-phalangeal joint with a device of the invention fitted, FIG. 3 illustrates a device of the invention having the convex surface radius greater than that of the concave surface, FIG. 4 is a diametral section through the device of FIG. 3, FIG. 5 illustrates the skeleton of a hand showing caps fitted to the metacarpo-phalangeal joints, and FIG. 6 illustrates a device of the invention having the radius of curvature of its convex surface of the same numerical value as the radius of curvature of the concave surface.

In the drawings and referring first to FIG. 1, 1 and 2 denotes bones the ends of which 1A and 2A respectively form together a metacarpo-phalangeal joint. The adjacent ends 1A and 2A of the bones 1 and 2 normally present smooth surfaces to one another with the convex radius of the surface 2A slightly less than the concave radius of the surface 1A. This difference in radius is usually present in joints such as metacarpo-phalangeal joints. although there are other joints in the human body which do not require to articulate through such a wide angle and where the two radii referred to approach more closely the same numerical value. The reason for the difference in radii is so that the surface of the bone end 2A in addition to sliding on the surface of the bone end 1A also rolls along the surface of the bone end 1A thereby reducing greatly the area of contact and thus the effort necessary to overcome the friction between the joint surfaces. The particular construction also promotes easier lubrication of the joint by the synovial fluid. When a joint becomes arthritic the rolling surfaces or sliding surfaces as the case may be become damaged and assume a configuration as is illustrated by the ragged lines 1B and 2B in FIG. 1. The pain associated with arthritis is caused by the asperities on the damaged surfaces rubbing over one another and is aggravated as the synovial fluid is forced out by the rubbing action.

In performing the method of the invention using the device of the invention the adjacent ends 1A and 2A of the bones are separated and the damaged cartilaginous surfaces 1B and 2B are ground away to remove all articular cartilage and dense bone and expose a portion of the bone tissue containing blood vessels so that a supply of blood is available. The new exposed surfaces are indicated by the interrupted lines 1C and 2C. Perichondrial grafts taken from another part of the same human body are laid over the exposed bone surfaces and sutured in position to cover the prepared surfaces. The perichondrial grafts are indicated at 1D and 2D. A cap 3 as illustrated in FIG. 3 having a convex surface 3A and a concave surface 3B is fitted over the bone end 2A enclosing the perichondrial graft 2D and the bones 1 and 2 are brought together so that the convex surface of the cap lies against the perichondrial graft covering the concave surface of the bone end 1A. The joint is now as illustrated in FIG. 2.

An interval of time is now allowed to elapse with the cap in position as illustrated. This interval of time is normally several weeks. At the end of the interval of time the perichondrium on both bone ends has formed cartilaginous surfaces in contact with the convex and concave surfaces of the cap. These cartilaginous surfaces have substantially the same composition as the original cartilaginous surfaces of the undamaged joint. The convex and concave surfaces 3A and 3B of the cap 3 act as moulds and cause the cartilage to form smooth surfaces of the same radii as the convex and concave surfaces of the cap and similar to the original surface. The bone ends are now again separated, the caps removed and the bone ends allowed to come together under the elastic action of the tendons and ligaments surrounding the joint. The joint rebuilt according to the invention and using the device of the invention can now be articulated pain-free or almost pain-free.

It may be remarked that after initial healing following insertion of a cap the joint may be articulated normally or substantially normally with the cap in place.

It has been found to be unnecessary to mould each cap for application to a specific joint because it has been found that only a comparatively restricted range of sizes of cap is required to fit almost all sizes of each type of joint, e.g. metatarsal joints, metacarpal joints, interphalangeal joints, likely to be encountered.

What is claimed is:

1. A method of repairing a human joint having damaged articular surfaces on the adjacent bone ends comprising separating the bone ends, removing enough of each bone end to expose a portion of the bone containing blood vessels, applying live perichondrial grafts taken from a bio-compatible donor over said exposed bone portions, applying a cap of concavo-convex lenticular form constructed of a bio-compatible flexible material between the grafts on the opposed bone ends such that the concave and convex surfaces will determine the contours of new opposed cartilaginous articular surfaces formed therealong and over the damaged surfaces, the concave and convex surfaces being such that no ingrowth of tissue takes place, bringing the bone ends against opposite sides of the cap, then after enough time has elapsed to permit the grafts to become permanent new cartilaginous surfaces on the bone ends and to mold themselves to the shape of the concave and convex surfaces respectively of the cap, separating the bone ends and removing the cap so that said new cartilaginous surfaces can come together by elastic action of the tendons and ligaments associated with the joint.

2. A method as claimed in claim 1 in which the radius of curvature of the convex surface and of the concave surface have the same numerical value.

3. A method as claimed in claim 1 in which the radius of the convex surface is greater than the radius of the concave surface.

* * * * *